United States Patent
Meijer et al.

[11] Patent Number: 6,022,344
[45] Date of Patent: Feb. 8, 2000

[54] CRYOPRESERVATION BAG

[75] Inventors: Else Johanna Meijer, Oldenzaal; Mirijam Wilhelmina Suzanna Ter Laak-Ter Beek, Almelo, both of Netherlands

[73] Assignee: NPBI International B.V., Emmer-Compascuum, Netherlands

[21] Appl. No.: 08/985,381

[22] Filed: Dec. 4, 1997

[51] Int. Cl.[7] .................................................. A61M 25/00
[52] U.S. Cl. .......................... 604/533; 604/403; 604/408; 604/415; 604/905; 128/DIG. 24; 128/DIG. 27
[58] Field of Search ..................................... 604/408, 409, 604/410, 403, 415, 533, 505; 283/381.4, 381.5; 128/DIG. 18, DIG. 24, DIG. 27

[56] References Cited

U.S. PATENT DOCUMENTS

| | | | |
|---|---|---|---|
| 3,576,650 | 4/1971 | Underwood et al. | 604/408 |
| 3,597,372 | 8/1971 | Cook | 260/4 |
| 3,741,253 | 6/1973 | Brax et al. | 138/137 |
| 3,839,743 | 10/1974 | Schwarcz | 604/7 |
| 3,963,026 | 6/1976 | Herb | 604/408 |
| 4,035,534 | 7/1977 | Nyberg | 428/36 |
| 4,131,200 | 12/1978 | Rinfret | 206/484 |
| 4,207,364 | 6/1980 | Nyberg | 428/36 |
| 4,212,299 | 7/1980 | Yokokoji et al. | 604/408 |
| 4,306,556 | 12/1981 | Zelman | 604/408 |
| 4,365,629 | 12/1982 | Pert et al. | 604/408 |
| 4,482,585 | 11/1984 | Ohodaira et al. | 428/35 |
| 4,516,977 | 5/1985 | Herbert | 604/415 |
| 4,561,110 | 12/1985 | Herbert | 604/408 |
| 4,588,402 | 5/1986 | Igari et al. | 604/408 |
| 4,837,047 | 6/1989 | Sato et al. | 422/41 |
| 4,917,804 | 4/1990 | Franks et al. | 210/737 |
| 4,950,347 | 8/1990 | Futagawa | 156/272.4 |
| 5,209,745 | 5/1993 | Irr et al. | 604/415 |
| 5,250,044 | 10/1993 | Irr et al. | 604/403 |
| 5,460,625 | 10/1995 | Johnson | 604/403 |

FOREIGN PATENT DOCUMENTS

| | | | |
|---|---|---|---|
| 2825014 | 12/1978 | France | 604/408 |

*Primary Examiner*—John G. Weiss
*Assistant Examiner*—Joseph K. Weiss, Jr.
*Attorney, Agent, or Firm*—Herbert Dubno

[57] ABSTRACT

The present invention relates to a bag for the cryopreservation of blood cells, comprising a joining piece and a shrink tube to connect the bag with a non-PVC tubing. The tubing is resistant to the liquid nitrogen temperature and can be used for RF sealing and sterile docking both before and after cryopreservation.

21 Claims, 12 Drawing Sheets

CRYOPRESERVATION BAG

FIELD OF THE INVENTION

The present invention relates to a novel bag for the cryopreservation of blood cells, comprising a joining piece and a shrink tube to connect the bag with non-PVC tubing. The tubing is resistant to liquid nitrogen temperature and can be used for RF sealing and sterile docking both before and after cryopreservation.

BACKGROUND OF THE INVENTION

In the art of blood transfusion some special blood components, such as stem cell preparations, are frozen in liquid nitrogen for long-term storage. For that purpose, after collecting and processing the blood in standard polyvinylchloride (PVC) bloodbags, the blood components are transferred into special cryopreservation bags, designed for storage in liquid nitrogen with a temperature of −196° C. When the blood components are needed for transfusion, the cryopreservation bag is taken out of the liquid nitrogen tank and thawed, usually by immersing it in a warm-water bath of about 37° C. After thawing and washing the blood components, transfusion into a patient can take place.

Among the currently available cryopreservation bags the preferred one is the Hemofreeze bag, supplied by NPBI International BV in the Netherlands. It is made of a laminate film that consists of a polyamide layer laminated with a fluoropolymer layer. Such a laminate film is for instance marketed under the name of Kapton®FN by the company DuPont de Nemours. The polyamide/fluoropolymer laminate film has proven its excellence for the cryopreservation of blood for many years now in the Hemofreeze cryopreservation bags. The use of this film for blood cryopreservation bags is also described in U.S. Pat. No. 5,209,745 and WO 91/11968 of IRR et al. However, the bags in these patents are equipped with ports to transfer the blood and therefore require aseptic handling with risk of contamination. The bags cannot be connected to other bags by sterile docking, a connection technique that is regarded as sterile in the art. Sterile docking is a thermal welding process wherein tubes of different bloodbag systems are welded together while the sterility of the resulting bloodbag system is maintained. Thus, the current cryopreservation bags made of polyamide/fluoropolymer laminate film cannot be used for sterile docking as they are not equipped with the tubing necessary for sterile docking.

Other currently available cryopreservation bags are equipped with sterile docking tubing, but this is usually polyvinylchloride. Polyvinylchloride is not resistant to very low temperatures, since it becomes brittle at these temperatures. Then cracking can occur or the polyvinylchloride can break during handling in frozen condition, leading to loss of the cell preparation and contamination of the freezer. Polyvinylchloride tubing on a cryopreservation bag can therefore be used for sterile docking to transfer blood into a cryopreservation bag, but has to be sealed and removed prior to subjecting the bag to the liquid nitrogen. (Sealing tubing means that the tubing is flattened at the desired spot and both sides of the flattened tubing are sealed together, thereby closing off the tubing's fluid path). After cryopreservation, transfer ports have to be used to transfer the blood out of the bag, thus requiring aseptic handling.

However, the use of aseptic transfer equipment, such as spikes and ports, to transfer blood components between bloodbags is the most important source of microbial contamination of blood. The internal fluid path of aseptic transfer equipment is exposed to the non-sterile environment as soon as the equipment is unpacked and opened for use. After bloodbag systems are connected by means of the transfer equipment, the blood flows through this non-sterile fluid path and can become contaminated. When blood is contaminated it must be regarded as unfit for human use and should be discarded. Thus, for a safe and efficient use of blood, contamination must be prevented and the methods used in transferring blood between bags must be as safe as possible. Therefore, the transfer of blood is preferably carried out in closed bloodbag systems where the tubing and bloodbags are connected in a sterile manner. Since the internal fluid path of a closed system is never exposed to the outer environment, the risk of microbial contamination is prevented and blood can be transferred between bags without losing its sterility. Closed, sterile bloodbag systems can be provided by sterile docking, carried out with sterile connection devices such as the Terumo SCD-312. Besides maintaining sterility, sterile docking also makes blood transfer between bags easier and more efficient. Thus, in order to prevent contamination during blood transfer, sterile docking is the preferred and in fact only possibility.

Tubes of blood collection and processing bags are usually made of polyvinylchloride. For cryopreservation bags however, other tubing materials have to be used since polyvinylchloride cannot be used at very low temperatures. Thus, the tubing of a cryopreservation bag is preferably not made of polyvinylchloride. However, the tubing has to be compatible with polyvinylchloride, since sterile docking is preferred for the transfer of blood from a polyvinylchloride bloodbag into the cryopreservation bag. Compatibility implies that the tubing material has to have a melting behavior comparable to that of polyvinylchloride and that the polymer chains of the two melted materials will mix at the contact surface. This can be established by subjecting the tubing to docking experiments with subsequent tests on tensile strength and leakage of the dock. Another requirement for the tubing of a cryopreservation bag is, of course, that it has to be resistant to the temperature of liquid nitrogen. This means that the material cannot be damaged by handling it at temperatures below its glass transition temperature and that it does not lose its specific properties after being cooled down to temperatures of −196° C. A third requirement for a cryopreservation bag tubing is that the tubing has the ability to be sealed by using conventional sealing technology, such as radio frequency (RF) sealing, as after transfer of the bag contents the tubing has to be closed off by sealing it.

Currently, all available cryopreservation bags lead to the same drawback: to transfer blood either to or from the bag, aseptic handling is necessary. There are no cryopreservation bags available with a sterile dockable and low temperature resistant tubing that can be used prior to as well as after cryopreservation to prevent aseptic handling and possible contamination. To overcome the drawbacks of the current cryopreservation bags, the preferred cryopreservation bag should be made out of polyamide/fluoropolymer laminate film and should have a sterile dockable and low temperature resistant tubing. The laminate film would ensure a good and proven performance of the bag at the liquid nitrogen temperature. The tubing would provide the possibility of a sterile and efficient transfer of blood between the cryopreservation bag and other bloodbags before and after cryopreservation by means of sterile docking, thus preventing contamination in the total process.

Unfortunately, such tubing cannot be connected properly to the desired film. To ensure a leaktight connection between the tubing and the polyamide/fluoropolymer laminate film, their connection should preferably be made by welding, which signifies that the heated materials are fused at their contact surface. Such a welded connection of two surfaces is called a seal. However, a sterile dockable tubing generally has a melting point that is considerably lower than the melting point of the fluoropolymer layer of the laminate film, which is the sealing layer of the film. Therefore, the required temperature for sealing the tubing to the film is too high and causes the tubing to melt before the fluoropolymer layer does. Adhesives to connect the film and tubing cannot be used either as fluoropolymers are anti-adhesive. Mechanical connections, where the materials are not fused as in a seal but are connected by a clamping force, mostly leave capillaries. These can cause leakage of fluids and gasses and therefore can cause contamination or loss of the bag contents. Therefore, a mechanical connection is only possible if it is properly leaktight. Thus although preferred, connecting a polyamide/fluoropolymer cryopreservation bag with a sterile dockable and low temperature resistant tubing without causing capillaries did not seem to be feasible up to now.

SUMMARY OF THE INVENTION

Our invention comprises a cryopreservation bag equipped with a non-PVC, sealable and liquid nitrogen temperature resistant tubing that can be used for sterile docking both before and after cryopreservation, the bag comprising a joining piece and a shrink tube to connect the bag with the tubing. The joining piece and shrink tube can provide a leaktight mechanical connection between the tubing and the bag. The mechanical connection is composed of two forces. First, the resilient nature of the tubing material provides an internal elastic force that causes the tubing to stay in place once it is pushed over the joining piece. Second, the shrink tube is shrunken around the tubing at the joining piece spot and provides an external clamping force on the tubing and joining piece. The addition of the shrink tube to the connection provides a stronger and leaktight connection. The shrink tube is thin walled to prevent influence on the cryopreservation process of the contents of the tubing and joining piece. Tests before and after cryopreservation have showed that a joining piece equipped with the tubing and shrink tube of this invention can endure a tensile force of one and a half up to twice as high as a joining piece and tubing without the shrink tube. Also, tests have showed that the connection made by means of the joining piece, tubing and shrink tube is gas-tight when subjected to an excess pressure by means of gas.

Specifically, the invention comprises a cryopreservation bag consisting of a body made of two sheets of polyamide/fluoropolymer laminate film with a joining piece sealed between these sheets and a section of non-PVC tubing assembled on the joining piece, the assembly being strengthened and tightened with a shrink tube. The cryopreservation bag is thus equipped with a tubing that is resistant to very low temperatures and that is sealable and sterile dockable both prior to and after being subjected to the liquid nitrogen temperature, providing the means for a safe transfer of blood to and from the bag in the total cryopreservation procedure and in this way preventing contamination. An example for the composition of such tubing is a blend of Hytrel© (commercially available from DuPont de Nemours) and Estane© (commercially available from B.F. Goodrich Chemical Co.), chemically known as thermoplastic polyester elastomer and thermoplastic polyurethane elastomer, in a ratio of respectively 80% and 20%.

The non-PVC tubing of the cryopreservation bag can be docked to PVC tubing of other bloodbags that contain blood that has to be cryopreserved. Once the blood is in the cryopreservation bag, the tubing is sealed at a certain distance from the entrance of the cryopreservation bag leaving enough length to the tubing for another sterile dock. The cryopreservation bag is now disconnected from the bloodbag and is ready to be frozen. Once the frozen blood is needed, the cryopreservation bag is taken out of the liquid nitrogen tank and thawed by immersion in a warm-water bath. With the remaining part of the tubing sterile docks with PVC tubing of another bloodbag system can be made and the blood can be transferred to that system in a safe, sterile manner.

As it must be able to withstand the liquid nitrogen temperature, the shrink tube in the preferred embodiment of the invention is made out of a fluoropolymer. The tubing is preferably made of a material with a resilient nature, such as the polymers that can be found in the group of thermoplastic elastomers, to provide the elastic clamping force of the tubing once it is assembled to the joining piece. The joining piece in the preferred embodiment is made of a fluoropolymer compatible to the fluoropolymer layer of the polyamide/fluoropolymer laminate film, to be able to seal the joining piece to the laminate film.

BRIEF DESCRIPTION OF THE DRAWING

FIG. 5 is a front view and FIG. 5a is a bottom view of the joining piece.

DETAILED DESCRIPTION

Figure 1:
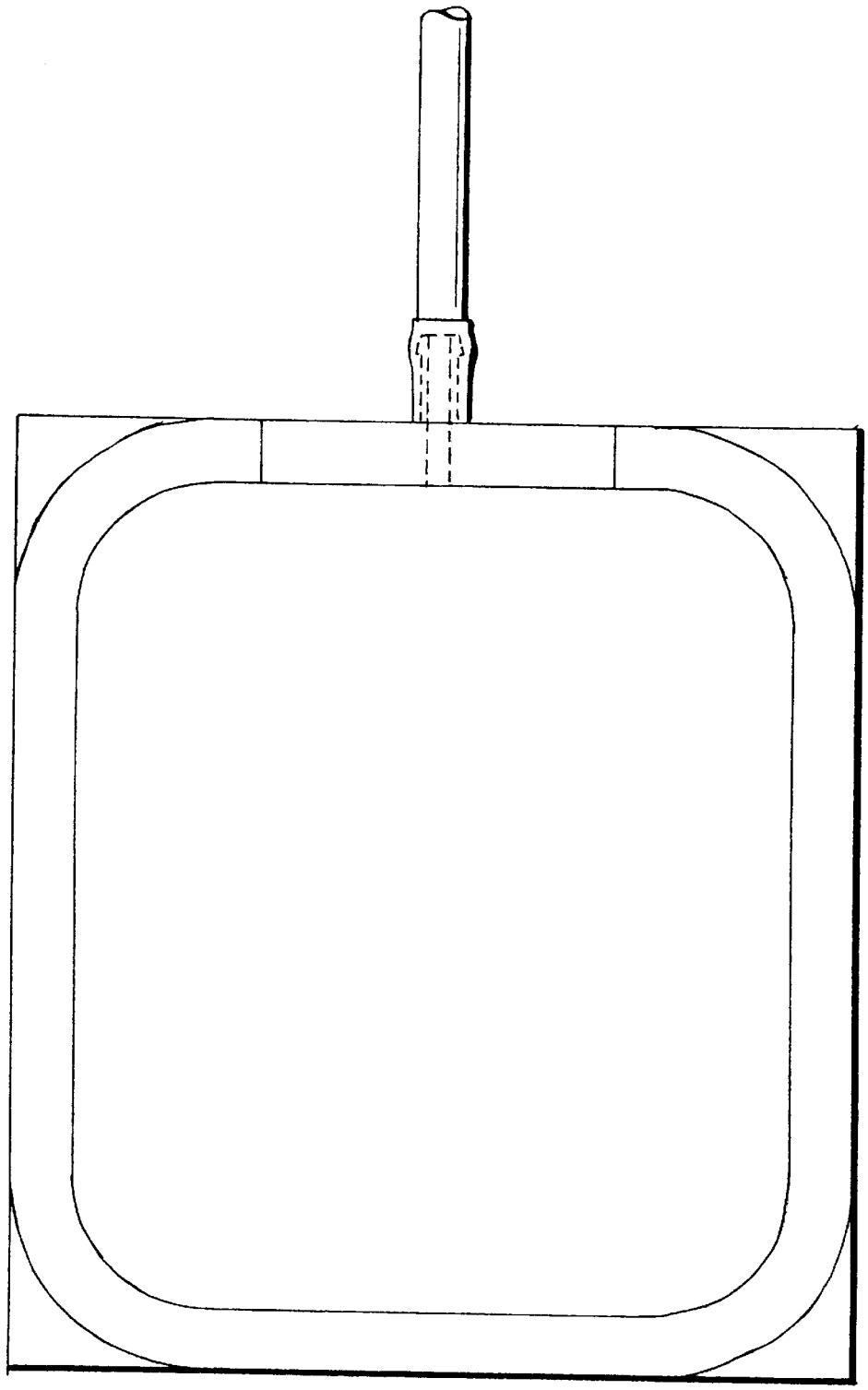
FIG. 1 is a plan view of the cryopreservation bag utilizing the invention.
Figure 2:
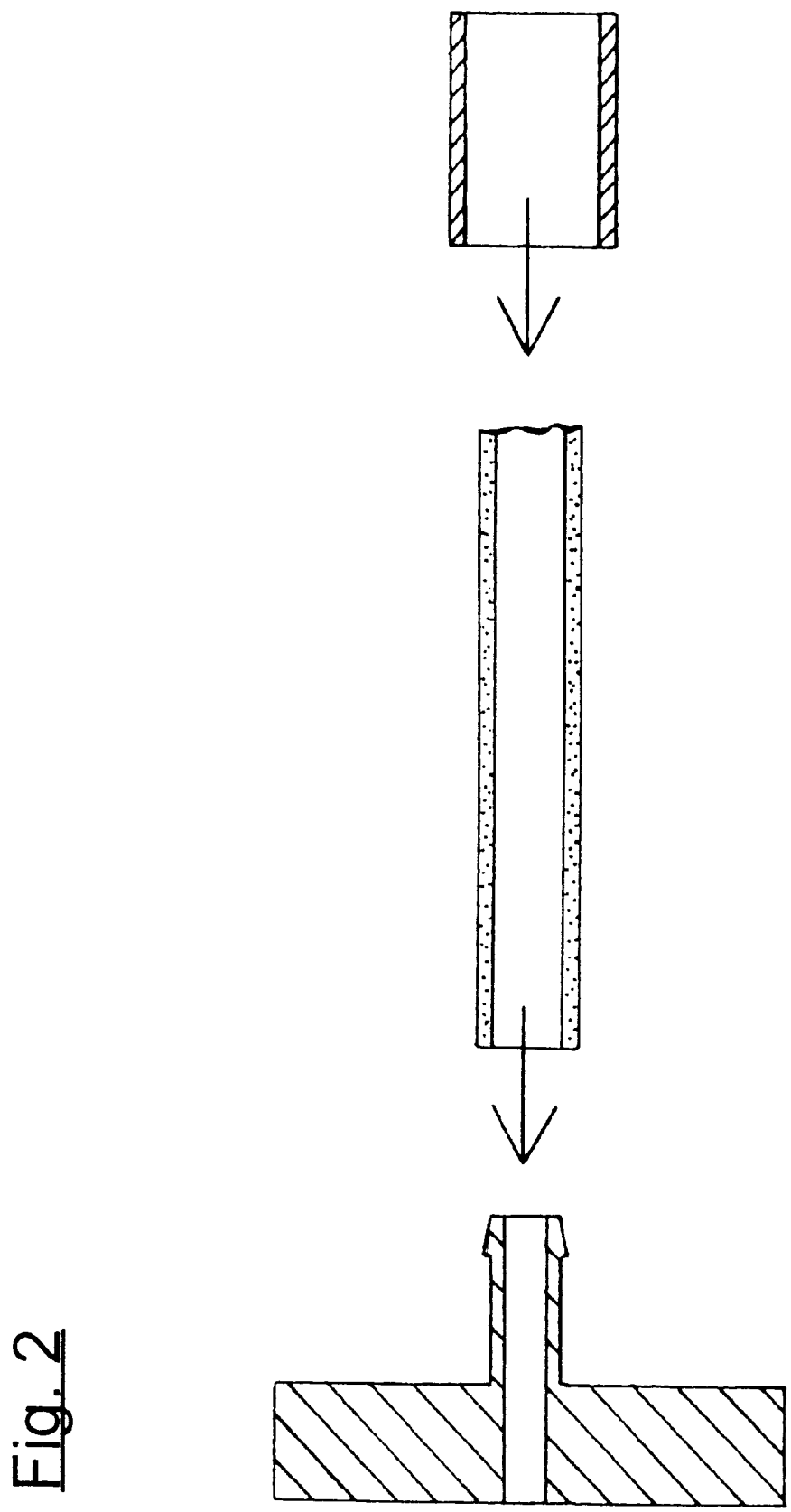
FIG. 2 is an exploded sectional view showing the assembly of the tubing and shrink tube to the joining piece.
Figure 3:
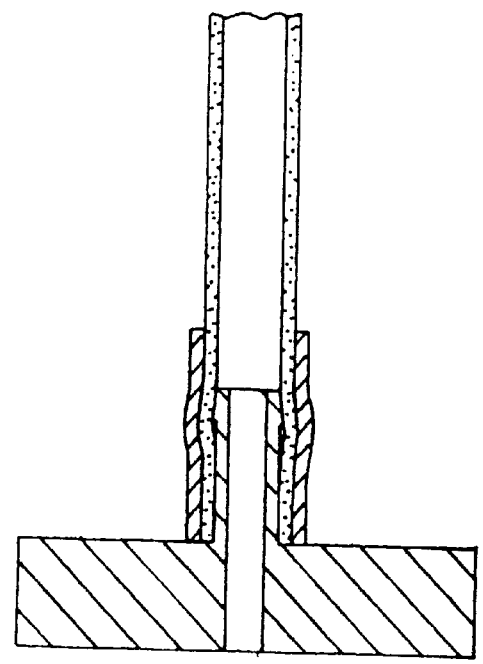
FIG. 3 is a sectional view showing the shrinking process of the shrink tube.
Figure 3:
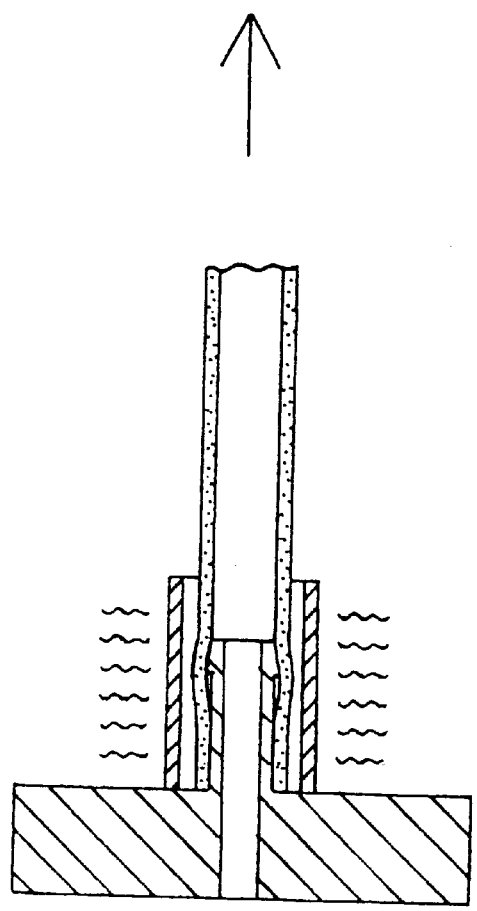
Figure 4:
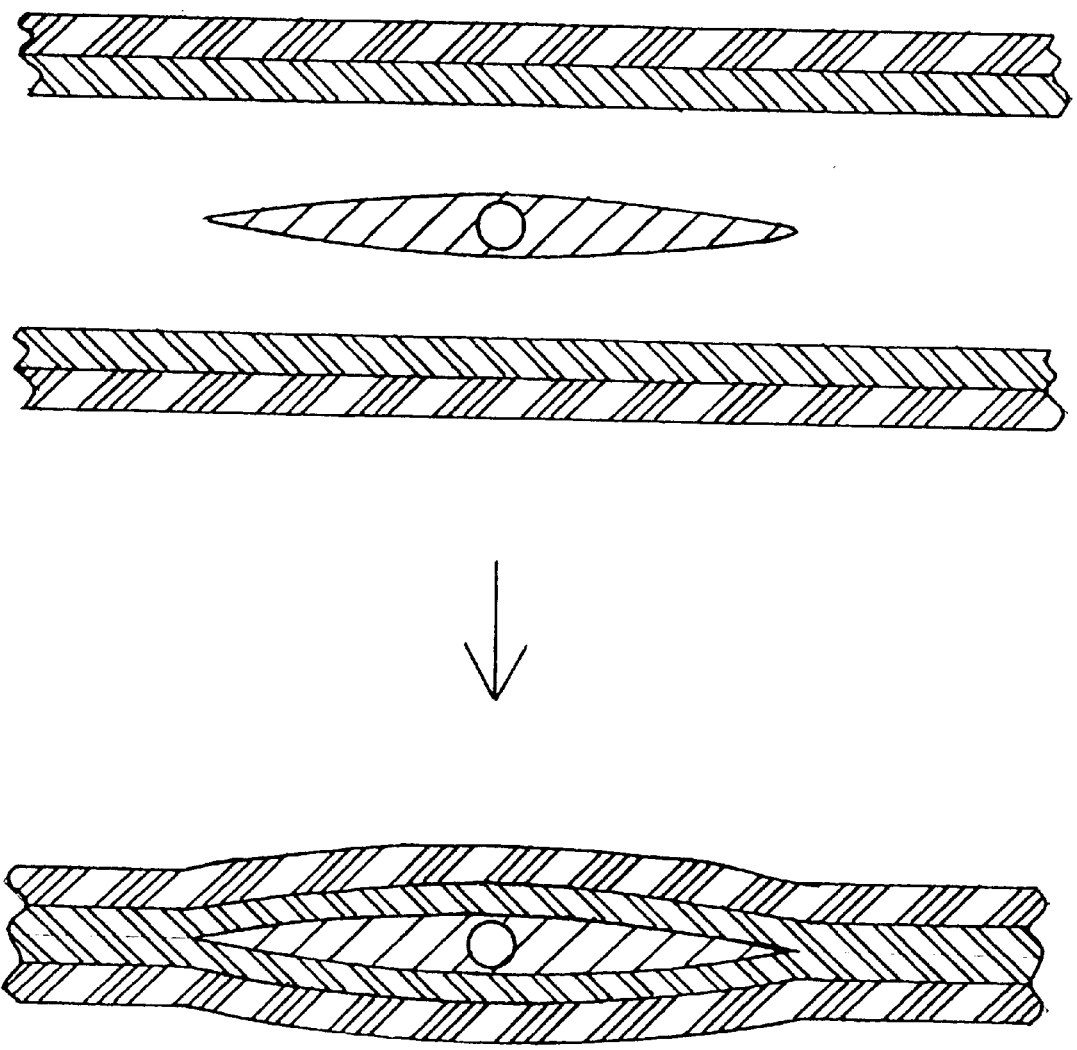
FIG. 4 shows the sealing process in which the joining piece of the invention is sandwiched between two sheets of film.

The invention provides a cryopreservation bag comprising a body 1 made of two layers of a polyamide/fluoropolymer laminate film 5. The tubing 3 is placed over the joining piece 2 and the shrink tube 4 is placed over the assembly of tubing and joining piece. FIG. 3 shows the shrinking process wherein the shrink tube 4 is heated to cause shrinkage. The joining piece 2 is sealed in between two sheets 5 of the laminate film, as can be seen in FIG. 4. The peripheral seal 6 that defines the dimensions of the bag is sealed separately. Therefore, many different shapes and dimensions of the cryopreservation bag are possible with the same invention. In an alternative embodiment the peripheral seal, that defines the dimensions of the cryopreservation bag, includes the seal for the joining piece which facilitates the production process.

In the preferred embodiment the shrink tube 4 is made of a fluorinated ethylene propylene copolymer to ensure liquid nitrogen temperature resistance. The shrink ratio of the shrink tube is 1.3 to 1. Its required shrink temperature is about 190° C., which is lower than the melting point of the sterile dockable, low temperature resistant tubing 3 to prevent this tubing from melting during the shrinking process.

Alternatively, the shrink tube can be made of other materials. Requirements for the shrink tube material are a proper resistance to very low temperatures, a shrink ratio between 1.1 to 1 up to and 6 to 1, and a shrink process (defined amongst others by heating temperature, heating time and cooling method of the assembly) that does not cause the tubing to melt during the process. Alternatively, the shrink tube can be made of other fluoropolymers, such as polytetrafluoroethylene, perfluoroalkoxy copolymers, or laminate shrink tubes made of two or more layers of said fluoropolymers.

The body 1 of the preferred cryopreservation bag is made of a polyamide film laminated with a fluoropolymer film. The fluoropolymer layer 7 is used to seal the film. The polyamide layer 8 provides the mechanical strength necessary at liquid nitrogen temperature, as unlike other plastics polyamide keeps its mechanical strength at −196° C., thus reducing the chance of damage to the bag or its contents. The polyamide/fluoropolymer laminate film has a low nitrogen permeability which is necessary as it is used in both liquid nitrogen and liquid nitrogen vapor. By means of the NPBI Hemofreeze cryopreservation bags, it has proven its suitability for cryopreservation applications.

Figure 5:
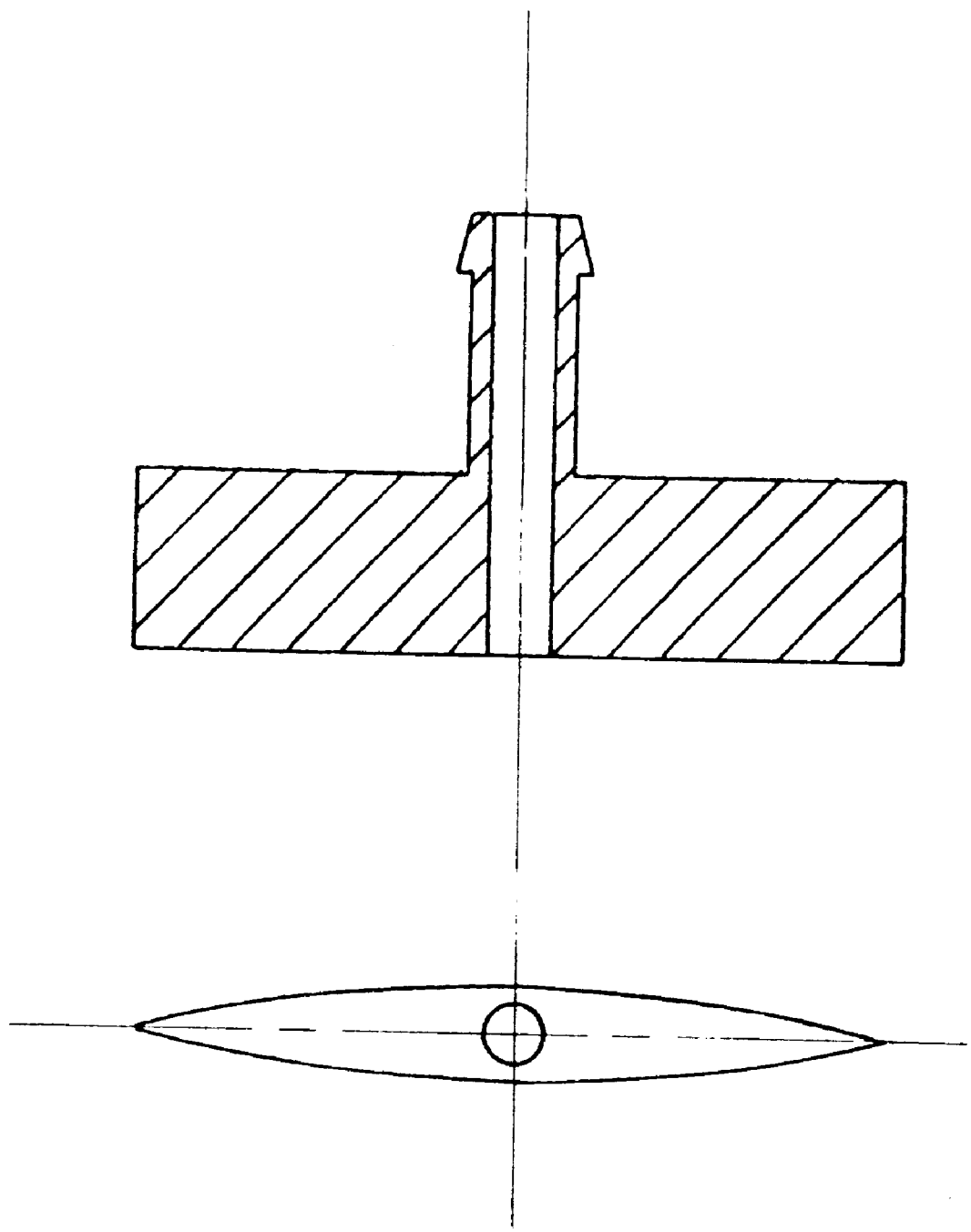

The joining piece 2 in the preferred embodiment is made of a perfluoroalkoxy copolymer, a fluoropolymer with properties comparable to the fluoropolymer layer 7 of the polyamide/fluoropolymer laminate film 5. Therefore, the materials are compatible and can be connected by means of sealing, thus providing a connection between the joining piece and the bag without capillaries. The shape of the preferred joining piece is optimized for sealing the joining piece into the laminate film, as its sealing surface 9 gradually changes from the tube size in the middle to a thin ending at the sides. The joining piece is equipped with a tube pillar 10 to assemble the tubing on it. The undercut 11 at the top of the pillar improves the tubing's resistance to shearing when a longitudinal force is applied to it (FIG. 5).

The tubing 3 in the preferred embodiment is made of a blend of thermoplastic polyester elastomer and thermoplastic polyurethane elastomer, compounded in a ratio of respectively 80% and 20%. This compound has the proper low temperature resistance and is sterile dockable to PVC tubes. Alternatively the ratio can be changed varying from approximately 55 up to and including 100% thermoplastic polyester elastomer and 0 up to and including approximately 45% thermoplastic polyurethane elastomer.

Figure 6:
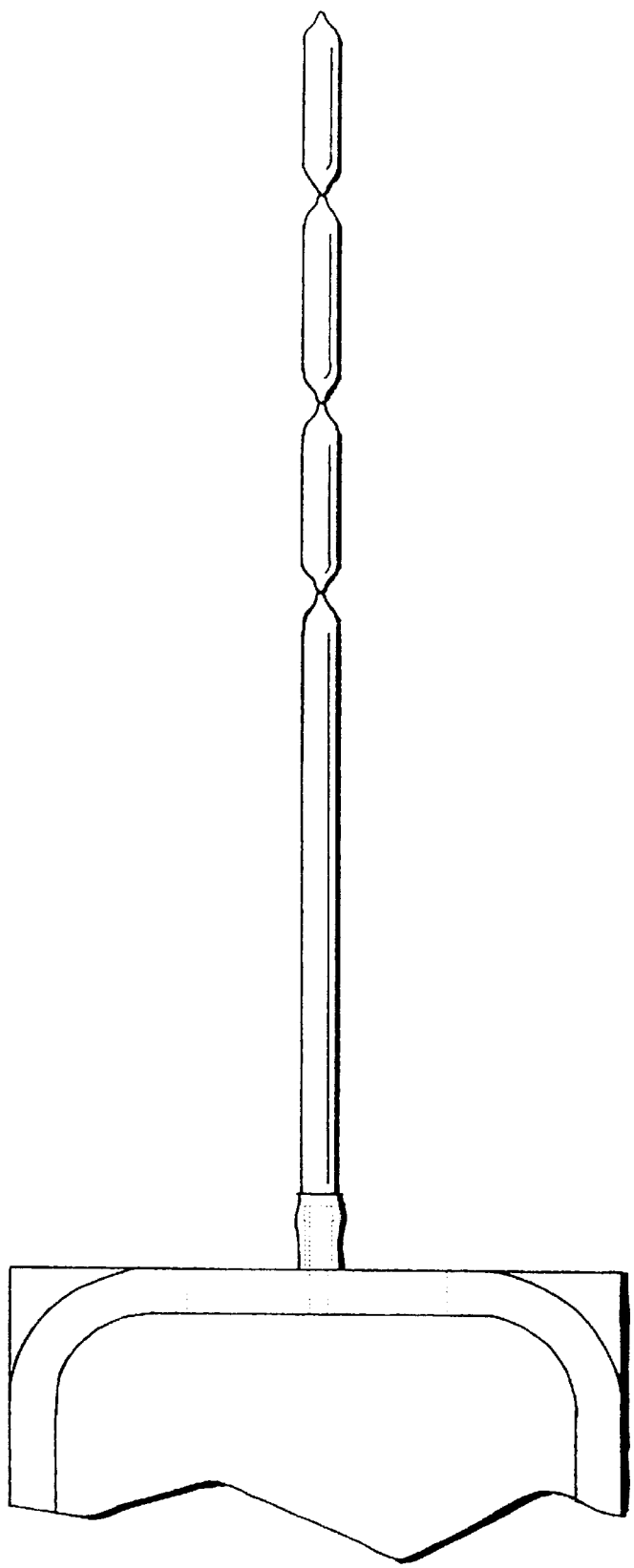
FIG. 6 is a fragmentary elevational view which shows sample segments that are sealed in the tubing.

The length of the tubing is designed so that several sterile docks as well as blood samples can be made with the tubing; after filling the cryopreservation bag, there is still blood remaining in the tubing. By means of sealing segments 12 in the tubing (FIG. 6) this blood can be used for samples. The samples can be frozen in liquid nitrogen. Leakage and tensile strength tests have showed that this tubing is both RF sealable and sterile dockable.

Figure 7:
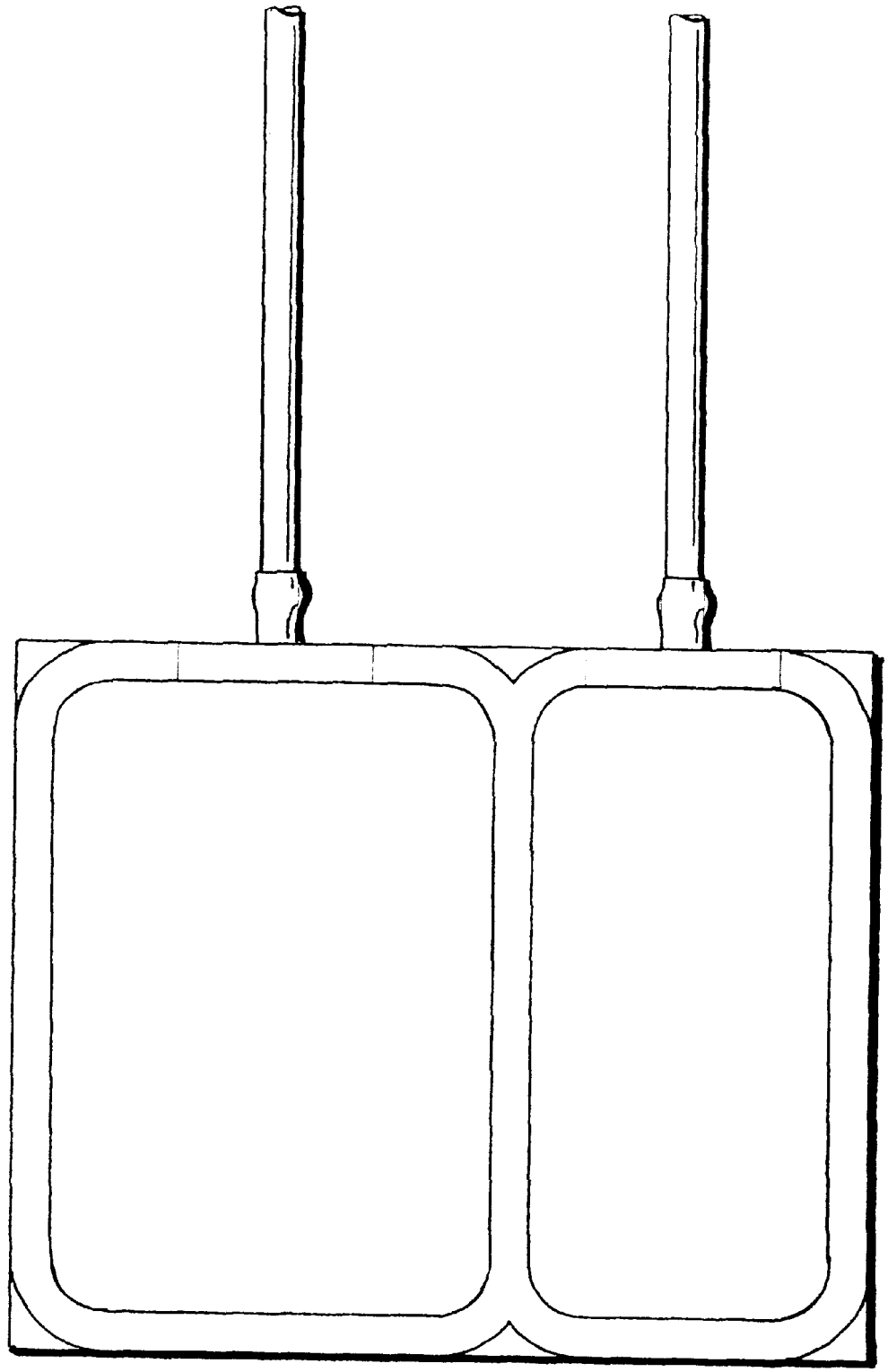
FIGS. 7, 8, 9 and 10 are plan views of alternative embodiments of the cryopreservation bag.
Figure 8:
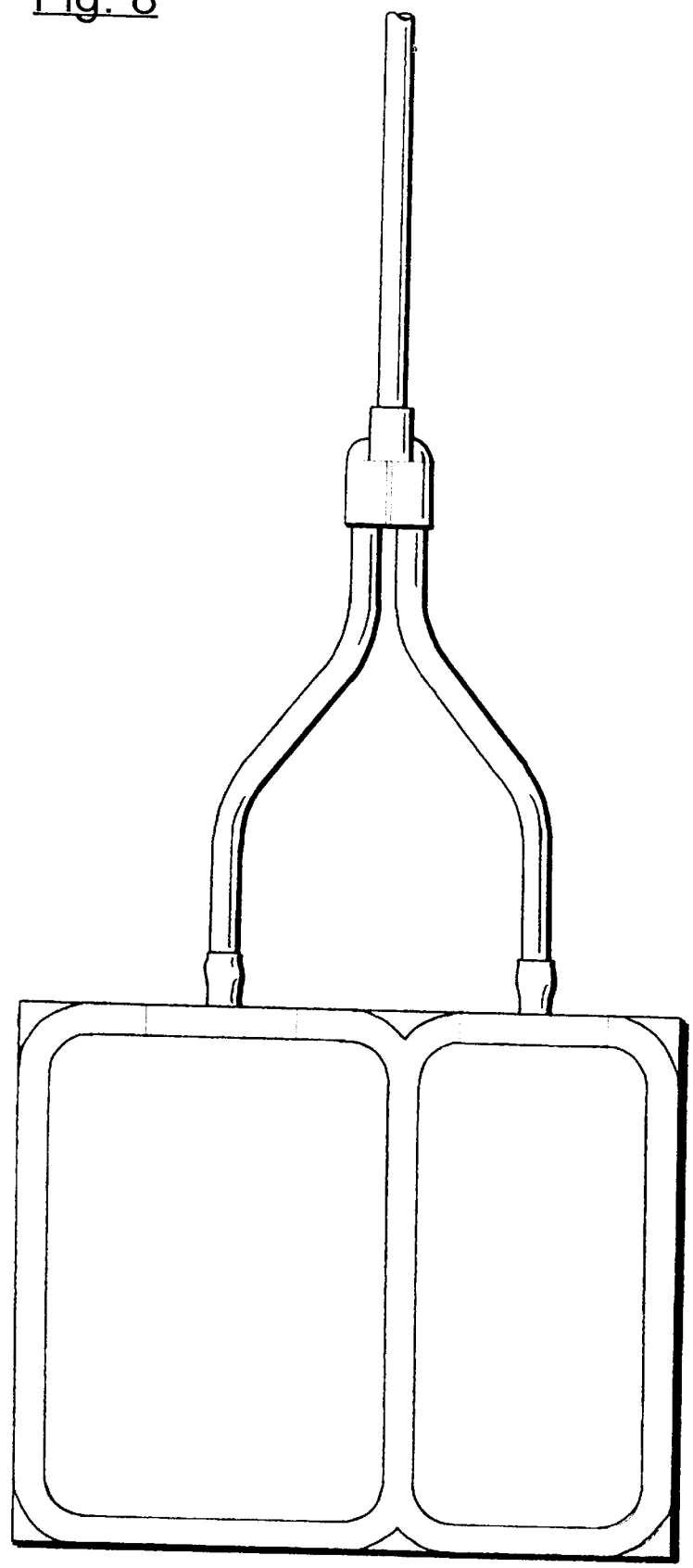

In an alternative embodiment (see, for example, FIG. 7) a cryopreservation bag 13 with two compartments 14 and 15 can be created by sealing two joining pieces into the film and adjusting the peripheral seal. To each joining piece a tubing can be assembled. These tubes can be used separately for blood transfer or the compartments can be attainable by connecting both tubes to a third tubing 16 (FIG. 8). In the same way, cryopreservation bags with more than two compartments can be created, still using the same invention.

Figure 9:
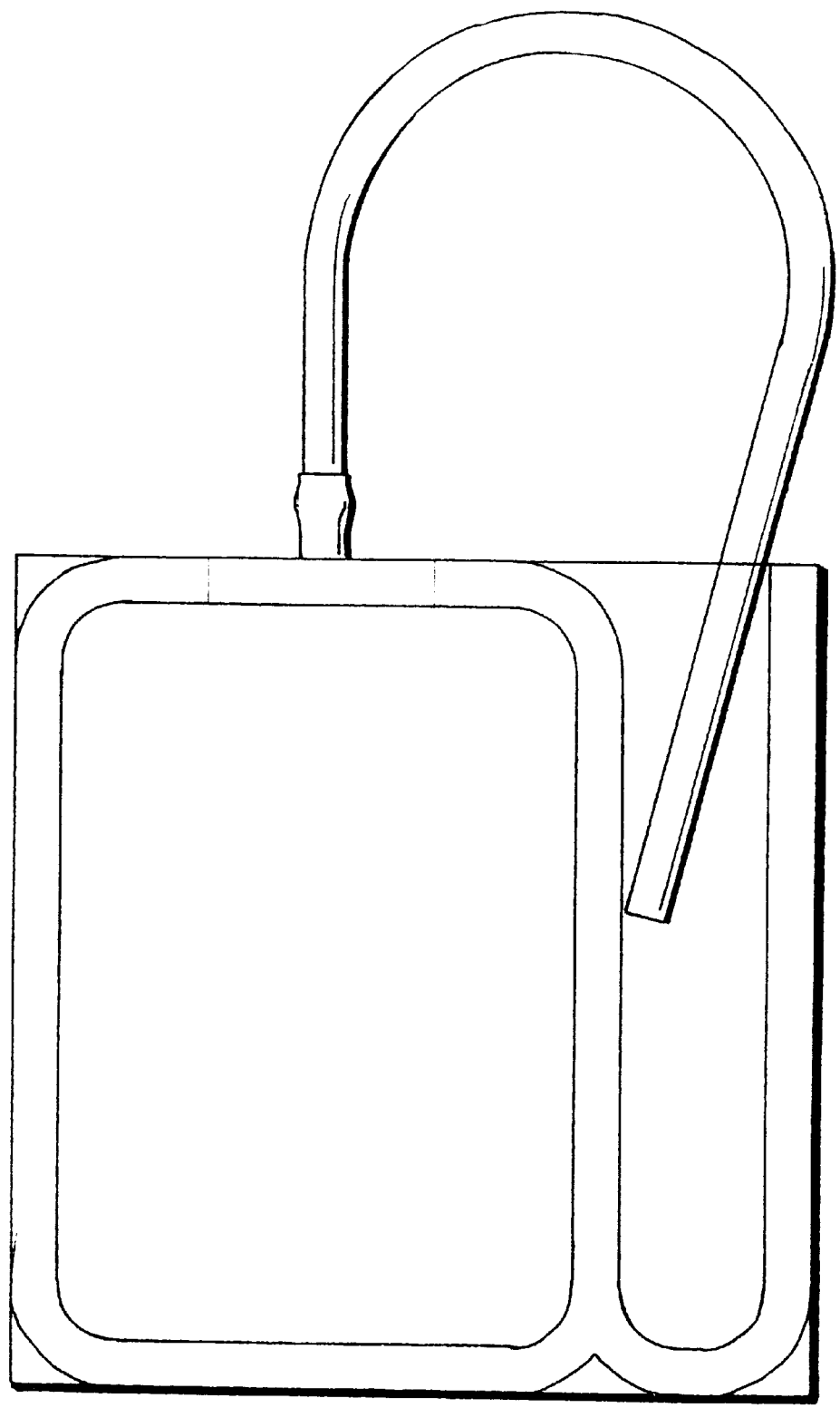
Figure 10:
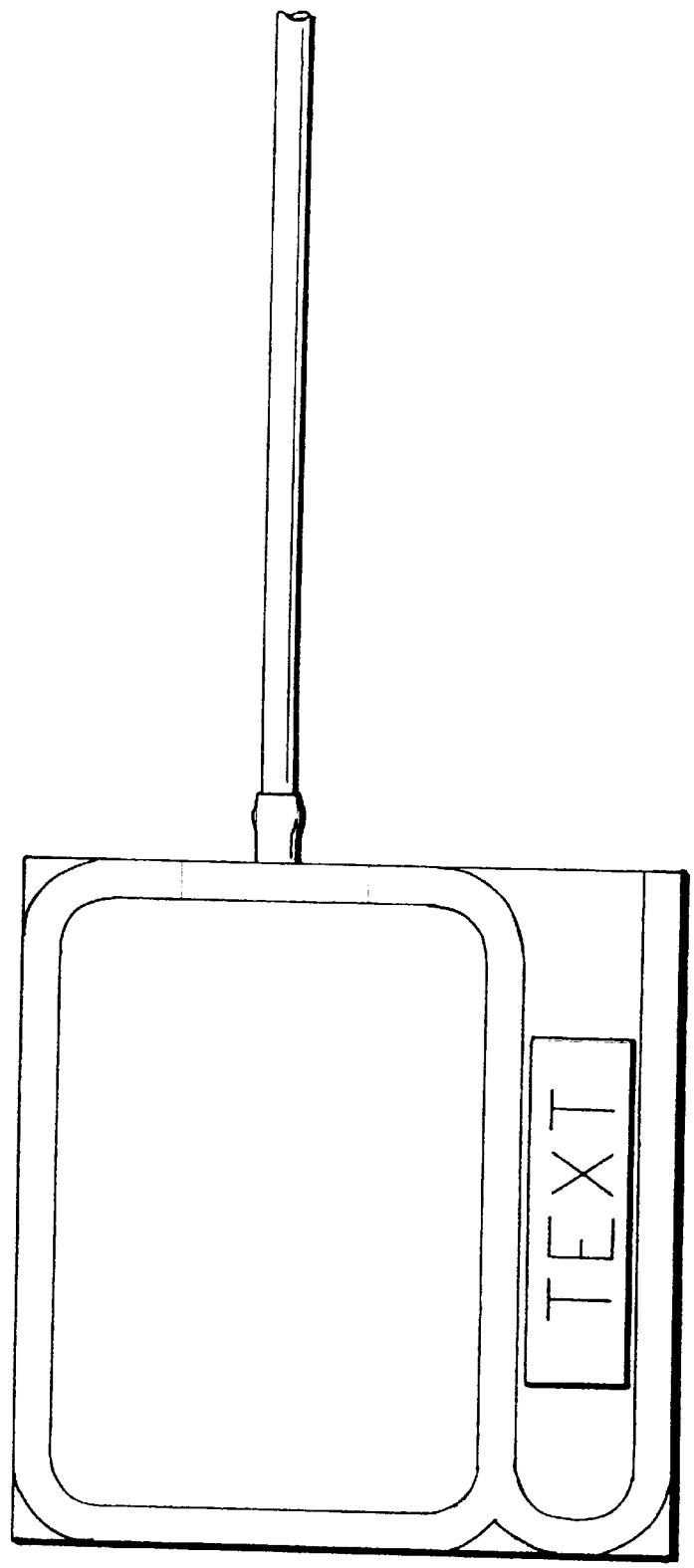
Figure 11:
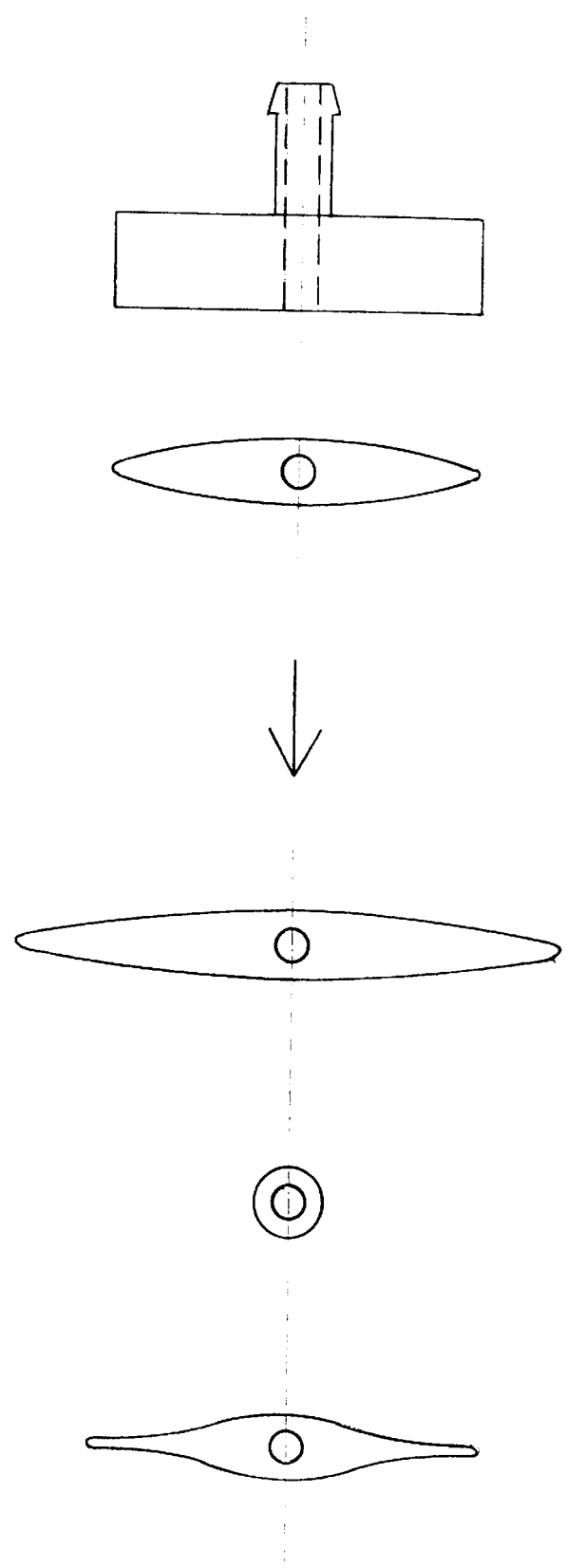
FIGS. 11A–11E show sectional views of several alternative embodiments of the joining piece's sealing surface.

Also, the cryopreservation bag can be equipped with an external pocket 17 (FIG. 9). The pocket can be used to store the tubing 3 during cryopreservation. In this way the total dimensions of the cryopreservation bag are more compact for storage in a liquid nitrogen tank, which saves costly storing space. The pocket 17 can also be used for labelling 18 of the contents of the cryopreservation bag, to be able to identify the blood transplant inside the bag (FIG. 10).

Figure 12:
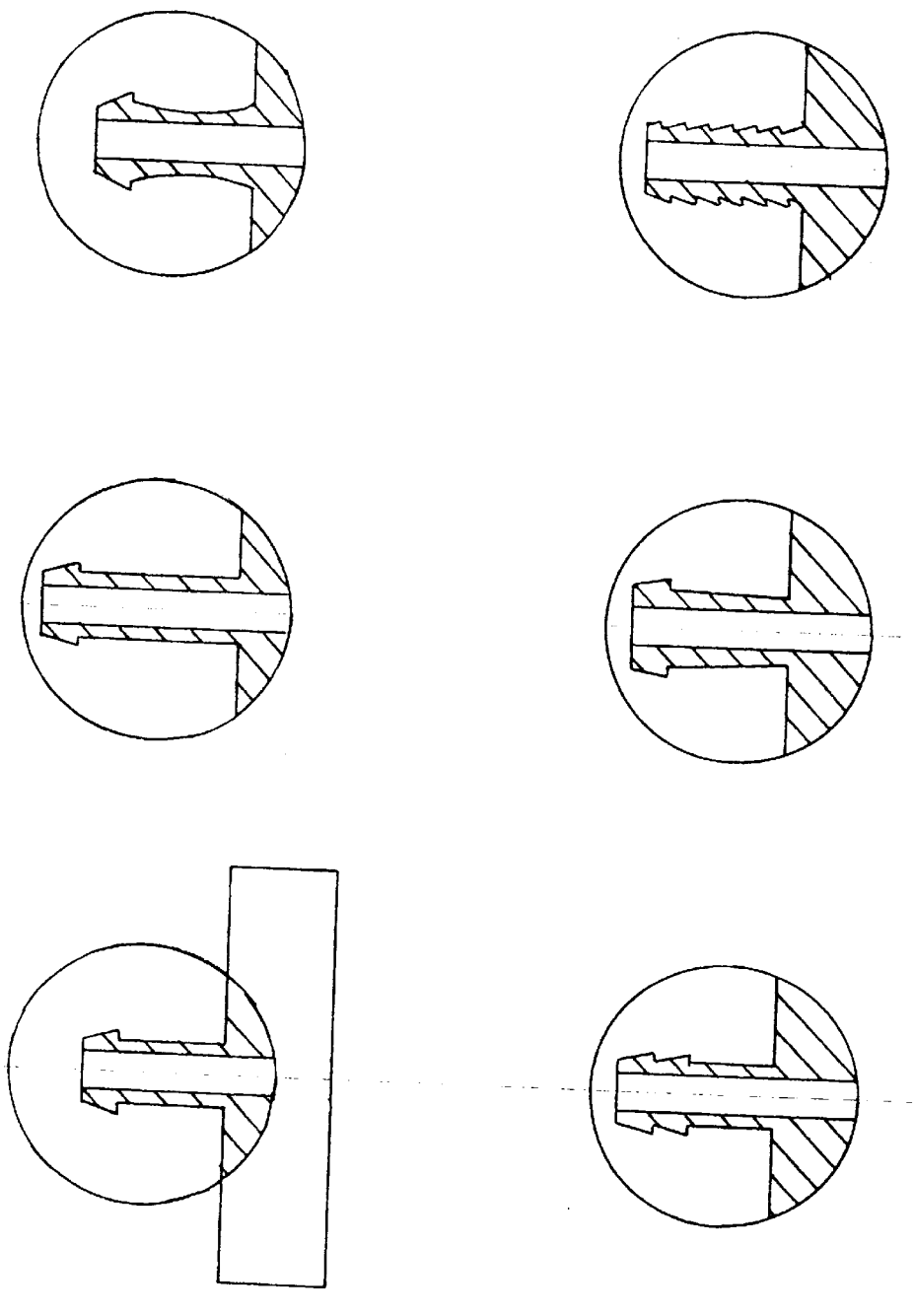
FIGS. 12A–12F show sectional views of several alternative embodiments of the joining piece's tube pillar.

In alternative embodiments (see FIGS. 11A–11E) the joining piece's dimensions can be changed as well, to optimize the sealing process for sealing the joining piece to the film. The sealing surface 19 can be made wider at 20 or more centric 21 or even can be somewhat shelved 22. Furthermore, the shape of the tube pillar 10 on the joining piece can be varied in length 23 (FIGS. 12A and 12B) or shape as at 24, 25, 26, 27 (see FIGS. 12C–12F) for a better assembly of the tubing to the pillar.

Besides the preferred compound for the tubing other materials can be used as well, as long as they meet the requirements for a sterile dockable, RF sealable and liquid nitrogen temperature resistant tubing. For instance the percentage of thermoplastic polyurethane elastomer that is added to the thermoplastic polyester elastomer can be varied. Also, thermoplastic polyamide elastomers can be used, as well as blends of thermoplastic polyamide elastomer with thermoplastic polyester elastomer or with thermoplastic polyurethane elastomers and blends with all three elastomers. To each elastomer or blend of elastomers additions of polyvinyl chloride or ethylene vinylacetate copolymers can be made to improve seal and dock properties of the polymer of polymer blend.

As can be concluded from all the mentioned preferred and alternative embodiments a very large variety of products can be created by using the original invention.

We claim:

1. A cryopreservation bag assembly, comprising a bag, a liquid nitrogen temperature resistant non-PVC tubing that can be used for RF sealing and sterile docking both before and after cryopreservation and connected to the bag, the bag further comprising a joining piece, an end of said tubing being fitted over said joining piece, and a shrink tube to connect the bag with the tubing, the shrink tube being fitted over said tubing on said joining piece, said tubing being made of a blend of at least two components selected from the group of components which consists of: thermoplastic polyester elastomers, thermoplastic polyurethane elastomers and thermoplastic polyamide elastomers in a common layer.

2. The bag assembly of claim 1 wherein said bag is made of a laminate film, consisting of a polyimide layer coated with a fluoropolymer layer.

3. The bag assembly of claim 1 wherein said shrink tube is made of a fluorinated ethylene propylene copolymer.

4. The bag assembly of claim 3 wherein said shrink tube has a shrink ratio of 1.3 to 1.

5. The bag assembly of claim 1 wherein said joining piece is made from a perfluoroalkoxy copolymer.

6. The bag assembly of claim 1 wherein said tubing is made of a blend of thermoplastic polyester elastomer and thermoplastic polyurethane elastomer in a ratio of approximately 80% thermoplastic polyester elastomer and approximately 20% thermoplastic polyurethane elastomer.

7. The bag assembly of claim 1 wherein said shrink tube is made of perfluoroalkoxy copolymer, polytetrafluoroethylene or another fluoropolymer.

8. The bag assembly of claim 1, wherein said shrink tube consists of two or more fluropolymer layers laminated together.

9. The bag assembly of claim 3 wherein said shrink tube has a shrink ratio in a range from 1.1 to 1 up to and including 6 to 1.

10. The bag assembly of claim 7 wherein said shrink tube has a shrink ratio in a range from 1.1 to 1 up to and including 6 to 1.

11. The bag assembly of claim 8 wherein said shrink tube has a shrink ratio in a range from 1.1 to 1 up to and including 6 to 1.

12. The bag assembly of claim 1 wherein said tubing comprises approximately 55 up to and including 100% thermoplastic polyester elastomer and 0 up to and including approximately 45% thermoplastic polyurethane elastomer.

13. The bag assembly of claim 1 wherein said tubing is made of a blend of thermoplastic polyester elastomer and thermoplastic polyamide elastomer.

14. The bag assembly of claim 1 wherein said tubing is made of a blend of thermoplastic polyurethane elastomer and thermoplastic polyamide elastomer.

15. The bag assembly of claim 1 wherein said tubing is made of a blend of thermoplastic polyester elastomer and thermoplastic polyurethane elastomer and thermoplastic polyamide elastomer.

16. The bag assembly of claim 6 wherein said blend of polymers comprises also polyvinylchloride or ethylene vinylacetate or polyvinylchloride and ethylene vinylacetate.

17. The bag assembly of claim 12 wherein said blend of polymers comprises also polyvinylchloride or ethylene vinylacetate or polyvinylchloride and ethylene vinylacetate.

18. The bag assembly of claim 13 wherein said blend of polymers comprises also polyvinylchloride or ethylene vinylacetate or polyvinylchloride and ethylene vinylacetate.

19. The bag assembly of claim 14 wherein said blend of polymers comprises also polyvinylchloride or ethylene vinylacetate or polyvinylchloride and ethylene vinylacetate.

20. The bag assembly of claim 15 wherein said blend of polymers comprises also polyvinylchloride or ethylene vinylacetate or polyvinylchloride and ethylene vinylacetate.

21. The bag assembly of claim 1 wherein said joining piece is made of fluorinated ethylene propylene copolymer or polytetrafluoroethylene or another fluoropolymer.

* * * * *